United States Patent
Sumiya et al.

(10) Patent No.: US 6,491,687 B1
(45) Date of Patent: *Dec. 10, 2002

(54) CORNEAL SURGERY APPARATUS

(75) Inventors: Toshifumi Sumiya, Nukata-gun; Mikio Arashima, Gamagori; Hidenori Kanda, Okazaki, all of (JP)

(73) Assignee: Nidek Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/249,133

(22) Filed: Feb. 12, 1999

Related U.S. Application Data

(60) Division of application No. 08/979,846, filed on Nov. 26, 1997, now Pat. No. 6,159,202, which is a continuation-in-part of application No. 08/714,809, filed on Sep. 17, 1996, now abandoned.

(30) Foreign Application Priority Data

Sep. 29, 1995 (JP) ............................................. 7-276327
Aug. 6, 1996 (JP) ............................................. 8-224509
Dec. 27, 1996 (JP) ............................................. 8-359005

(51) Int. Cl.⁷ .................................................. A61G 9/18
(52) U.S. Cl. ................................ 606/5; 606/3; 606/10; 606/11; 351/211
(58) Field of Search .......................... 606/2, 4–6, 10, 606/11, 17, 18; 351/205, 209, 210, 211

(56) References Cited

U.S. PATENT DOCUMENTS

| | | | |
|---|---|---|---|
| 4,443,075 A | | 4/1984 | Crane |
| 4,848,340 A | * | 7/1989 | Bille et al. ................ 606/4 |
| 5,098,426 A | * | 3/1992 | Sklar et al. ................ 606/4 |
| 5,410,376 A | * | 4/1995 | Cornsweet et al. ........ 351/210 |
| 5,507,799 A | | 4/1996 | Sumiya |
| 5,562,656 A | | 10/1996 | Sumiya |
| 5,632,742 A | | 5/1997 | Frey et al. |
| 5,684,562 A | * | 11/1997 | Fuyieda ................... 351/211 |
| 6,159,202 A | * | 12/2000 | Sumiya et al. ............ 606/4 |

FOREIGN PATENT DOCUMENTS

| | | |
|---|---|---|
| DE | 42 32 021 | 4/1994 |
| WO | WO 93/16631 | 9/1993 |
| WO | WO 94 18883 | 9/1994 |

* cited by examiner

*Primary Examiner*—David M. Shay
(74) *Attorney, Agent, or Firm*—Oliff & Berridge PLC

(57) ABSTRACT

An ophthalmic surgery apparatus comprising a system for observing an anterior portion of an eye, and an optical system for irradiating a laser beam for treatment to the eye, the apparatus is a corneal surgery apparatus irradiating the laser beam to a cornea and ablating a surface thereof, the apparatus comprising a moving device for moving the optical system relatively against the eye, an illuminating device for illuminating a large area of the anterior portion of the eye, a photoelectric transducing device having a two-dimensional light sensing plane, for sensing distribution of light volume of the anterior portion of the eye, a pupil position sensing device for sensing the position of a pupil, a control device for controlling the moving device based on sensed results, a tracking signal generating device for generating a signal to track movement of the eye, whereby the moving device is controlled by the control device so as to track movement of the eye by inputting a signal generated by the tracking signal generating device, and a device for prohibiting irradiation of the laser beam in the case that the position of the pupil misses the predetermined limits.

10 Claims, 10 Drawing Sheets

POSITION OF THE CENTER OF GRAVITY
(THE CENTER OF PUPIL)

LINE A-A

CORNEAL SURGERY APPARATUS

This is a Division of application Ser. No. 08/979,846 filed Nov. 26, 1997, now U.S. Pat. No. 6,159,202, which in turn is a Continuation-In-Part of application Ser. No. 08/714,809, filed Sep. 17, 1996, now abandoned. The entire disclosure of the prior applications are hereby incorporated by reference herein in its entirety.

BACKGROUND OF THE INVENTION

1. Field of the Invention

The present invention relates to an ophthalmic surgery apparatus which treats by irradiating a laser beam to an eye of a patient, and more particularly to a mechanism for delivering the laser beam to a desired position of the eye and for tracking movement of the eye.

2. Description of the Related Art

As an ophthalmic surgery apparatus which treats by irradiating a laser beam to an eye of a patient, for example, a corneal surgery apparatus which uses an excimer laser beam is known. This apparatus ablates a surface of a cornea by irradiating the excimer laser beam so as to remove a diseased portion of the cornea and corrects an ametropia by changing a curvature of the cornea.

In the case that this apparatus is used, an operator makes the patient fix a fixation target with the eye, then aligns an irradiating optical system with the eye so as to be desired condition with observing an alignment target. The alignment is completed, then the operator makes this apparatus irradiate the laser beam so as to ablate determined amount of a desired area of the eye.

Though the patient is made to fix the fixation target with the eye, if an eyeball of the eye happens to move during the alignment or the laser beam irradiation and the movement is confirmed by the operator, then the operator must do the alignment over again once more from beginning, or the operator must discontinue the laser beam irradiation and do the alignment over again.

As described above, doing the alignment over again is a burden to both the patient and the operator because of taking much a long time for its operation or the like. Furthermore, in the case that the eyeball moves often, the burden is much more.

And if the operator does not notice the movement of the eyeball and continues the laser beam irradiation, then the cornea is not ablated so as to be an expected shape, therefore a refractive power of the eye after the operation is influenced thereby.

Furthermore, if the operator is not accustomed to operating the apparatus, then the alignment itself takes much time.

SUMMARY OF THE INVENTION

The present invention has been made in view of the above circumstances and has an object to overcome the above problems, and to provide an ophthalmic surgery apparatus, which may make it easy to align a laser beam irradiating optical system with an eye of a patient without burdening both a patient and an operator.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic surgery apparatus comprising an observation optical system for observing an anterior portion of an eye of a patient, and a laser beam irradiating optical system for irradiating a laser beam for treatment to the eye, the ophthalmic surgery apparatus is a corneal surgery apparatus irradiating the laser beam to a cornea of the eye and ablating a surface of the cornea, the apparatus comprises a moving means for moving the laser beam irradiating optical system relatively against the eye, an illuminating means for illuminating a large area of the anterior portion of the eye, a photoelectric transducing means having a two-dimensional light sensing plane, for sensing distribution of light volume of the anterior portion of the eye illuminated by the illuminating means, a pupil position sensing means for sensing the position of a pupil by processing the signal transmitted by the photoelectric transducing means, a control means for controlling the moving means based on results sensed by the pupil position sensing means, a tracking signal generating means for generating a signal to track movement of the eye, whereby the moving means is controlled by the control means so as to track movement of the eye by inputting a signal generated by the tracking signal generating means, and an irradiation prohibiting means for prohibiting irradiation of the laser beam in the case that the position of the pupil misses the predetermined limits.

In another aspect of the present invention, an ophthalmic surgery apparatus comprising an observation optical system for observing an anterior portion of an eye of a patient, and a laser beam irradiating optical system for irradiating a laser beam for treatment to the eye, the ophthalmic surgery apparatus is a corneal surgery apparatus irradiating the laser beam to a cornea of the eye and ablating a surface of the cornea, the apparatus comprises a moving means for moving the laser beam irradiating optical system relatively against the eye, an illuminating means for illuminating a large area of the anterior portion of the eye, a photoelectric transducing means having a two-dimensional light sensing plane, for sensing distribution of light volume of the anterior portion of the eye illuminated by the illuminating means, a pupil position sensing means for dividing a sensing area of the photoelectric transducing means into the predetermined number, then sensing the position of a pupil based on analysis and comparison for light-and-shade information of the divided respective areas, a pupil position sensing means divides the two-dimensional sensing plane into at least more than four members, then senses the position of a pupil based on bias of the light-and-shade which is obtained every divided area, and a control means for controlling the moving means based on results sensed by the pupil position sensing means.

In another aspect of the present invention, an ophthalmic surgery apparatus comprising an observation optical system for observing an anterior portion of an eye of a patient, and a laser beam irradiating optical system for irradiating a laser beam for treatment to the eye, the ophthalmic surgery apparatus is a corneal surgery apparatus irradiating the laser beam to a cornea of the eye and ablating a surface of the cornea, the apparatus comprises a moving means for moving the laser beam irradiating optical system relatively against the eye, an illuminating means for illuminating a large area of the anterior portion of the eye, a photoelectric transducing means having a two-dimensional light sensing plane, for sensing distribution of light volume of the anterior portion of the eye illuminated by the illuminating means, a pupil position sensing means for dividing a sensing area of the photoelectric transducing means into the predetermined number, then sensing the position of a pupil based on analysis and comparison for light-and-shade information of the divided respective areas, a pupil position sensing means including a light-and-shade sensing means for dividing the two-dimensional light sensing plane into some number which have areas not adjacent each other, then obtaining the light-and-shade information every the divided area, a judging means for judging whether there is difference of the predetermined light-and-shade degree in the light-and-shade information of areas not adjacent each other and a pupil position specifying means for specifying that the pupil exists in dark side area in the case that the judging means judges that there is the difference of the predetermined light-and-shade degree and a control means for controlling the moving means based on results sensed by the pupil position sensing means.

Further, in another aspect of the present invention, an ophthalmic surgery apparatus further comprises a threshold level determining means for determining a threshold level for use in specifying a pupil area, and wherein the pupil position sensing means senses the position of the pupil based on the threshold level determined by the threshold level determining means and the signal of distribution of light volume transmitted by the photoelectric transducing means.

According to the present invention, it is capable of preventing an irradiating area from deviating, and is capable of treating an eye of a patient appropriately, because the apparatus can track the eye even if an eyeball of the eye moves during the laser beam irradiation. Also, a stable tracking can be realized with reducing an effect caused by a noise light.

Furthermore, since the performance for operating is improved, so burden is allowed to be decreased for both the patient and the operator. Furthermore, the trouble of the alignment is allowed to be decreased, therefore the alignment adjustment can be performed easily.

BRIEF DESCRIPTION OF THE DRAWINGS

The present invention will be described with reference to the accompanying drawings in which.

DETAILED DESCRIPTION OF THE PREFERRED EMBODIMENTS

One preferred embodiment according to the present invention will be now described with reference to the accompanying drawings.

[General Construction]

Figure 1:
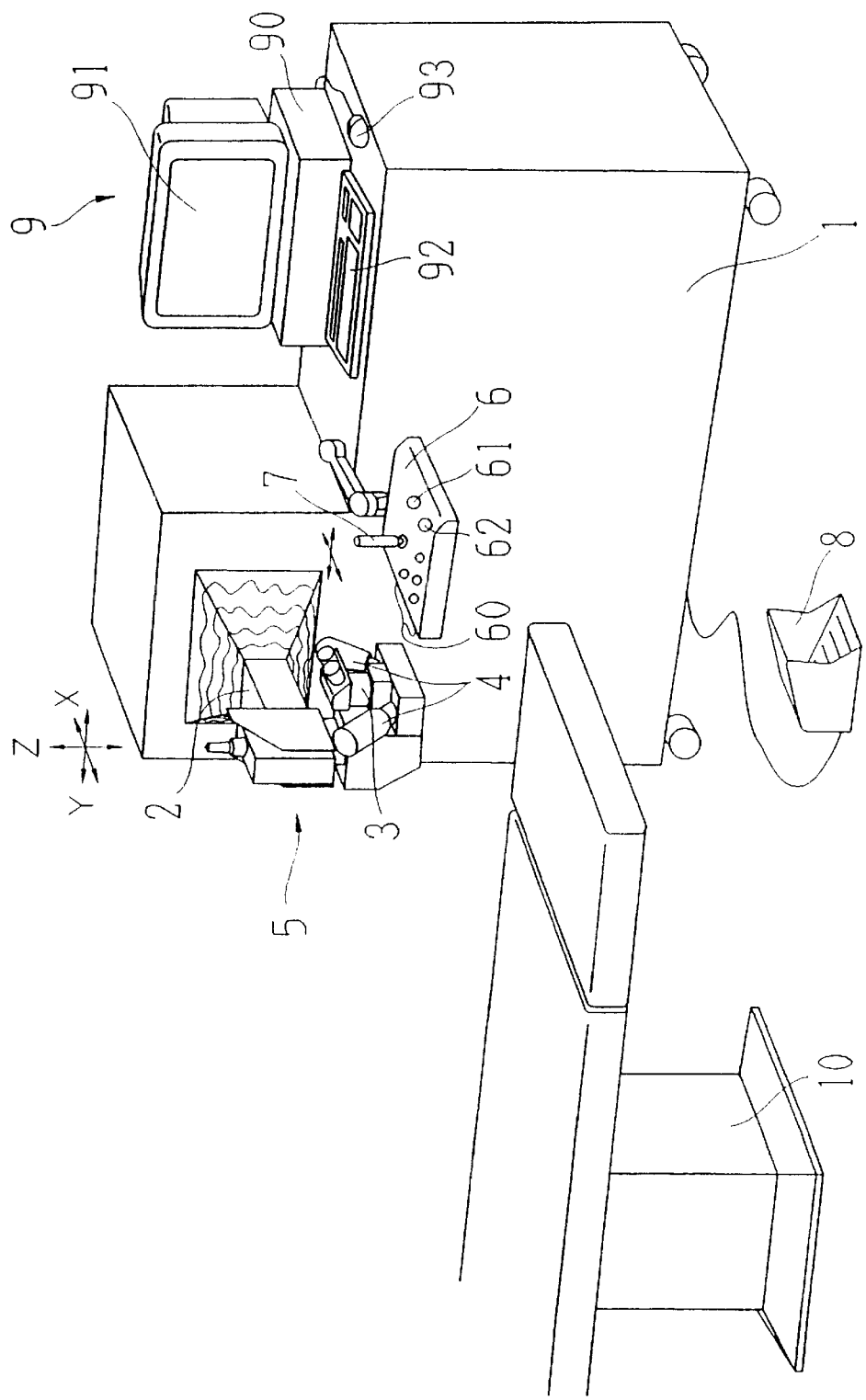
FIG. 1 is an external view showing a whole schematic configuration of an apparatus for a corneal surgery according to the preferred embodiment of the present invention.

FIG. 1 is an external view showing a schematic construction of an apparatus for a corneal surgery by using an excimer laser beam. Reference numeral 1 indicates a primary body of a surgery apparatus, in which an excimer laser beam source and the like are contained. The laser beam irradiated from the excimer laser beam source is reflected by mirrors inside the body 1, then is delivered to an arm part 2. An edge part of the arm part 2 is provided with an observation optical part 5 including a binocular microscope 3 for observing a patient's eye 15, an illumination part 4, a laser beam irradiating orifice not shown, an eyeball position detecting optical system mentioned-below or the like. The illumination part 4 is provided with a visible-rays illumination light source which emits a light within a range of visible-rays, used for that an operator observes the patient's eye, and an IR-rays illumination light source 20 which emits a light within a range of infrared-rays for use in detecting position of an eyeball mentioned-below.

Figure 2A:
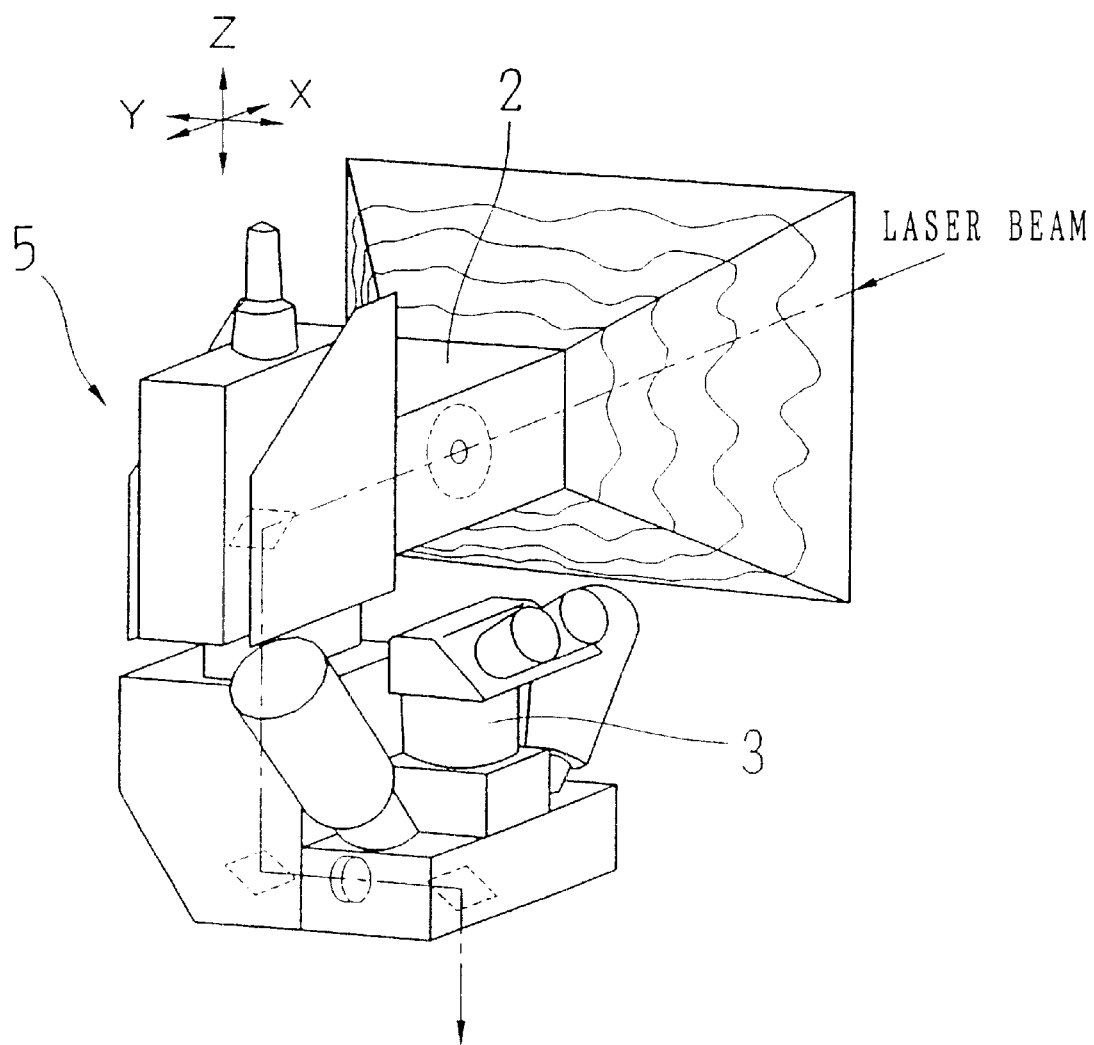
FIG. 2A is a view showing optical elements arrangement of inside of an arm part of an apparatus.
Figure 2B:
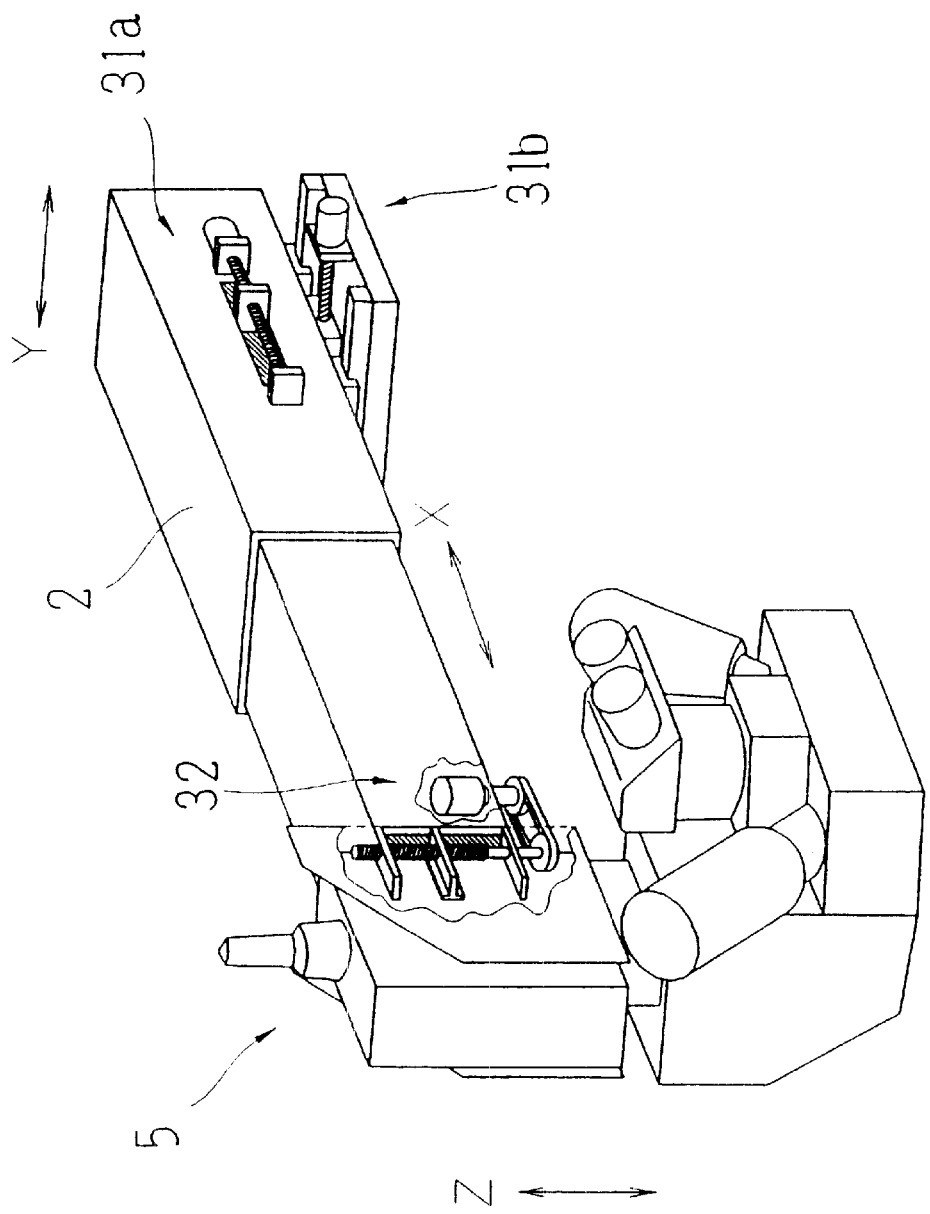
FIG. 2B is a view showing movement mechanism of an arm part.

The laser beam is delivered to the patient's eye by some optical elements such as mirror disposed inside the arm part 2 and the observation optical part 5 (see FIG. 2A). As shown in FIG. 2B, the arm part 2 moves in X-direction (lateral direction to the operator) under control of a X-direction arm driving device 31a and moves in Y-direction (forward and backward directions to the operator) under control of a Y-direction arm driving device 31b. Also, the observation optical part 5 moves in Z-direction (direction of a laser beam irradiating optical axis) under control of a Z-direction arm driving device 32. Respective arm driving devices 31a, 31b and 32 consists of a motor, a sliding mechanism or the like.

Reference numeral 6 indicates a controller, which includes a joystick 7 for giving a signal for driving the arm part 2 in X,Y-directions, and several kinds of operating switches such as a focus-adjusting switch 60 for performing an alignment of Z-direction, an automatic alignment switch 61 for desiring a change between ON and OFF of an automatic alignment, a Ready switch 62 for changing its state from stand-by to such state as being capable of irradiating the laser beam. Reference numeral 8 indicates a foot switch for sending a laser emission signal, and 9 indicates a computer for inputting some kinds of necessary data of operating condition, for calculating, displaying, storing the laser irradiating data, or the like. The computer 9 consists of a primary body 90, a monitor 91, a keyboard 92, a mouse 93 or the like. Reference numeral 10 is a bed to make the patient lie down thereon.

[Constructions of Respective Components]

(Optical System)

Figure 3:
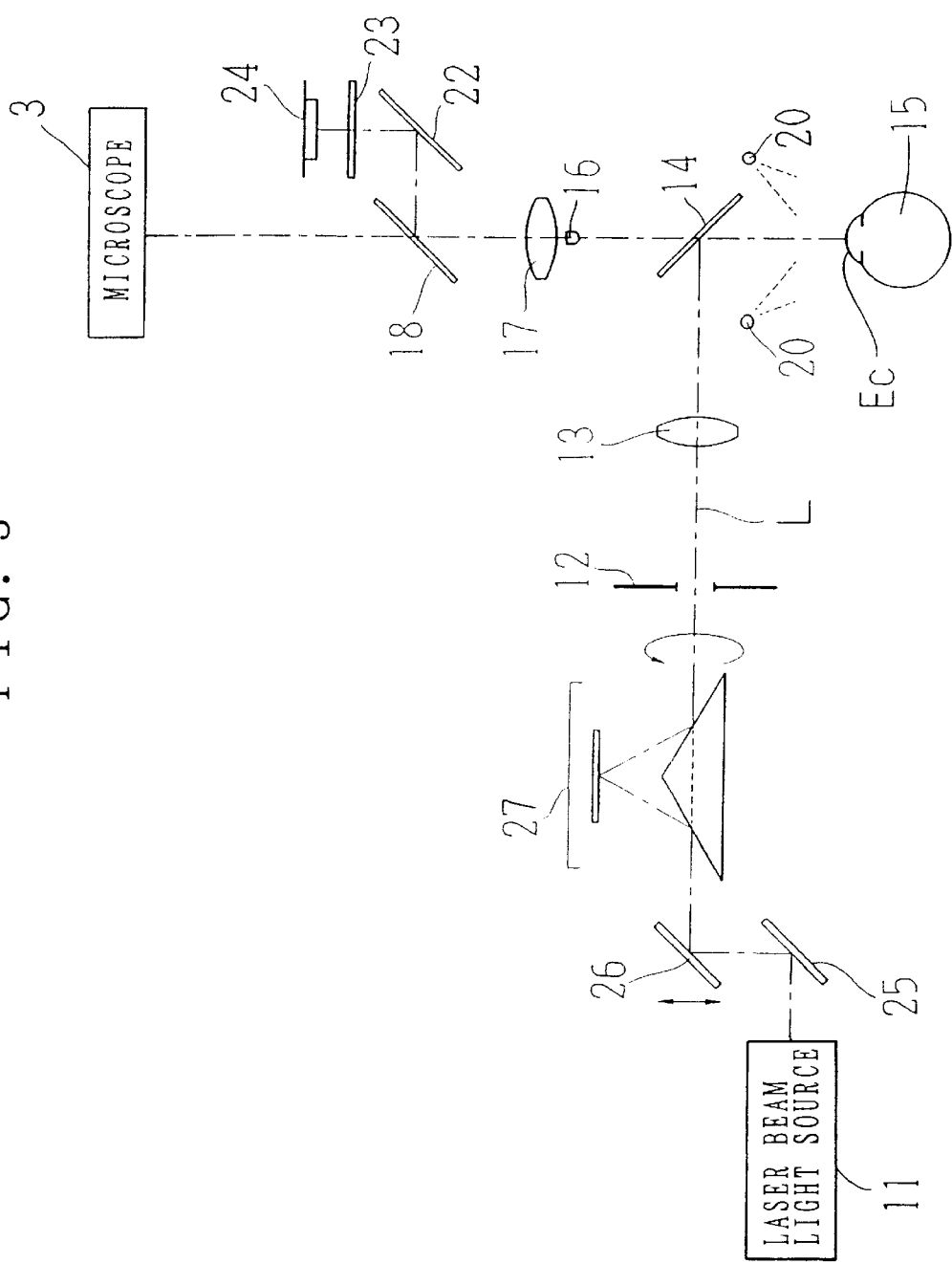
FIG. 3 is a schematic view showing an optical system of an apparatus of the preferred embodiment of the present invention.

FIG. 3 is a schematic view showing an optical system of the apparatus of the preferred embodiment.

(A) Laser Beam Irradiating Optical System

Reference numeral 11 indicates the laser beam source for irradiating the excimer laser beam of 193 nm wave length. 25 indicates a plane mirror capable of reflecting the laser beam, which is emitted by the laser beam source 11 to horizontal direction, to upper direction of 90 degrees. 26 indicates a plane mirror capable of moving to vertical direction (denoted by an arrow), which causes the laser beam to be polarized to horizontal direction once more. 27 indicates an image rotator which causes the laser beam to rotate around an optical axis L (the laser beam irradiating optical axis). 12 indicates an aperture for limiting an irradiating area of the laser beam, of which the aperture diameter is can be changed by an aperture driving device not shown. 13 is a projection lens for projecting the aperture 12 onto a cornea Ec of the patient's eye 15. The aperture 12 is located on a conjugate position with the cornea Ec via the projection lens 13, and the area limited by the aperture 12 is projected onto the cornea, thereby the area of keratectomy (ablation) is limited. The laser beam having a rectangular cross section irradiated from the laser beam source 11 moves to the predetermined direction based on parallel movement of the mirror 26, and covers whole area of the aperture 12. Ablation performed by controlling movement of the mirror 26 and an opening-degree of the aperture 12 are disclosed in Japanese Patent Laid-Open No. HEI4-242644 (corresponding to U.S. Pat. No. 5,507,799) to be referred.

Reference numeral 14 indicates a dichroic mirror having such characteristics that reflects the excimer laser beam and transmits the visible-rays and the infrared-rays, enabling the optical axis of the laser beam irradiating optical system to coincide with an optical axis of an objective lens of an observation optical system mentioned-below. In the case of coinciding with a guide light on the light source side, the dichroic mirror 14 is made to have characteristics reflecting a part of the guide light.

(B) Observation Optical System

Reference numeral 17 indicates the objective lens, 18 indicates a dichroic mirror having characteristics of transmitting the visible-rays and of reflecting the infrared-rays. An image of an anterior portion of the patient's eye 15, which is illuminated by the visible illumination light from the visible-rays illumination light source not shown, is transmitted to the microscope 3 via the dichroic mirror 14, the objective lens 17 and the dichroic mirror 18. The operator observes the patient's eye 15 by using the microscope 3. A reticle plate not shown is inserted into the observation optical system and the reticle plate can be the standard for the alignment in X,Y-directions of the patient's eye 15.

Also, an target projecting system composed of two slits (see Japanese Patent Laid-Open No. HEI6-47001 corresponding to U.S. Pat. No. 5,562,656) is disposed in the observation optical system in order to perform the alignment in Z-axis direction. 16 indicates a fixation lamp placed on the optical axis of the objective lens 17.

(C) Eyeball Position Detecting Optical System

Reference numeral 20 indicates the IR-rays illumination light source such as LED which emits the light within the range of near infrared-rays or the like, and 4 members of the IR-rays illumination light sources 20 are disposed at intervals of 90 degrees each other around the optical axis. 22 is a reflecting mirror, 23 is an IR-rays transmitting filter, and 24 is a CCD camera having sensitivity within the range of near infrared-rays. A photo-imaging plane of the CCD camera 24 is arranged so as to be approximately conjugate with a position close to a pupil of the patient's eye 15 with respect to the objective lens 17.

The image of the anterior portion of the patient's eye 15 illuminated by the IR-rays illumination light source 20 is formed on the photo-imaging plane of the CCD camera 24 via the dichroic mirror 14, the objective lens 17, the dichroic mirror 18, the reflecting mirror 22 and the IR-rays transmitting filter 23. At this moment, the IR-rays transmitting filter 23 cuts slightly the visible-rays reflected by the dichroic mirror 18. A signal of the image photographed by the CCD camera 24 is inputted to a control device 30 mentioned-below.

Figure 4:
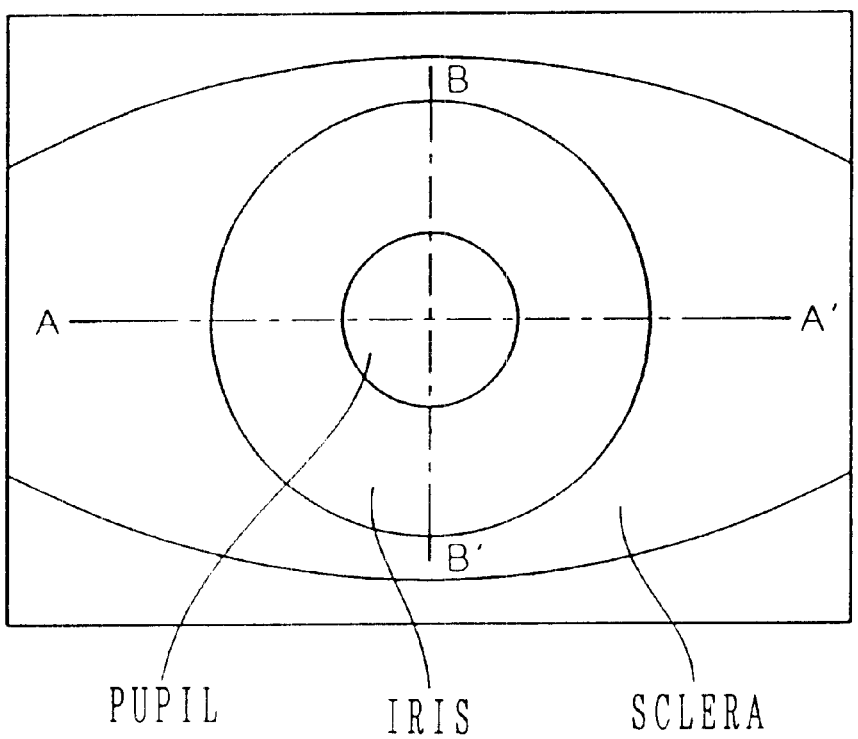
FIG. 4 is a view showing an image of an anterior portion of an eye of a patient photographed by a CCD camera.
Figure 5:
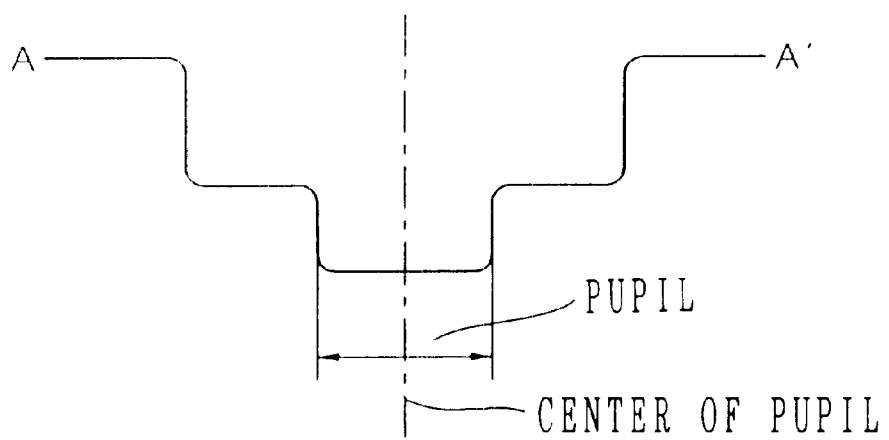
FIG. 5 is a view showing distribution of light volume on line A–A' shown in FIG. 4.

The CCD camera 24 detects the eyeball position as following. FIG. 4 shows the image of the anterior portion of the patient's eye 15 photographed by the CCD camera 24, and FIG. 5 shows a view of distribution of light volume on line A–A' (FIG. 4) based on the image signal from the CCD camera 24. As shown in figures, the respective light volumes are different by which a pupil, an iris, a sclera, therefore according to this information, pupil edge coordinates in lateral direction can be detected, furthermore, in accordance with detection of the pupil edge, the center position, so called, a pupil center coordinate in lateral direction is can be obtained. In the same way as is described, the pupil center coordinate in longitudinal direction can be obtained by using information of distribution of light volume on longitudinal line B–B'. Therefore, in accordance with both of them, the pupil position relative to the optical axis of the detecting optical system (so called the optical axis of the laser beam irradiating optical system), which is regulated so as to be the predetermined positional relationships on the photo-imaging elements of the CCD camera 24, is obtained. Still, the lateral and longitudinal detecting lines are preferably to be averaged in response to the information concerning distribution of light volume of plural lines with the center at the middle of the photo-imaging elements of the CCD camera 24.

Furthermore, if the processing time permits, the position of the center of gravity may be obtained based on the whole pupil area.

In addition, the light by corneal reflection of the IR-rays illumination light source 20 is also transmitted to the CCD camera 24, however if the IR-rays illumination light source 20 is arranged so that a corneal reflex may not interrupt the detecting lines (lateral and longitudinal), then the light by corneal reflection is prohibited from becoming noise light at the time when positional coordinates are to be detected. That is, the line linked by two opposite light sources is made to slant to 45 degrees relative to the detecting lines (lateral and longitudinal), and is made so that the image of the light source may be formed at periphery side of the cornea. Besides, the preferred embodiment does not restricted by such composition of above-mentioned arrangement, therefore various changes and modifications may be made as far as the pupil edge (or the iris) can be detected.

(D) Control System

Figure 6:
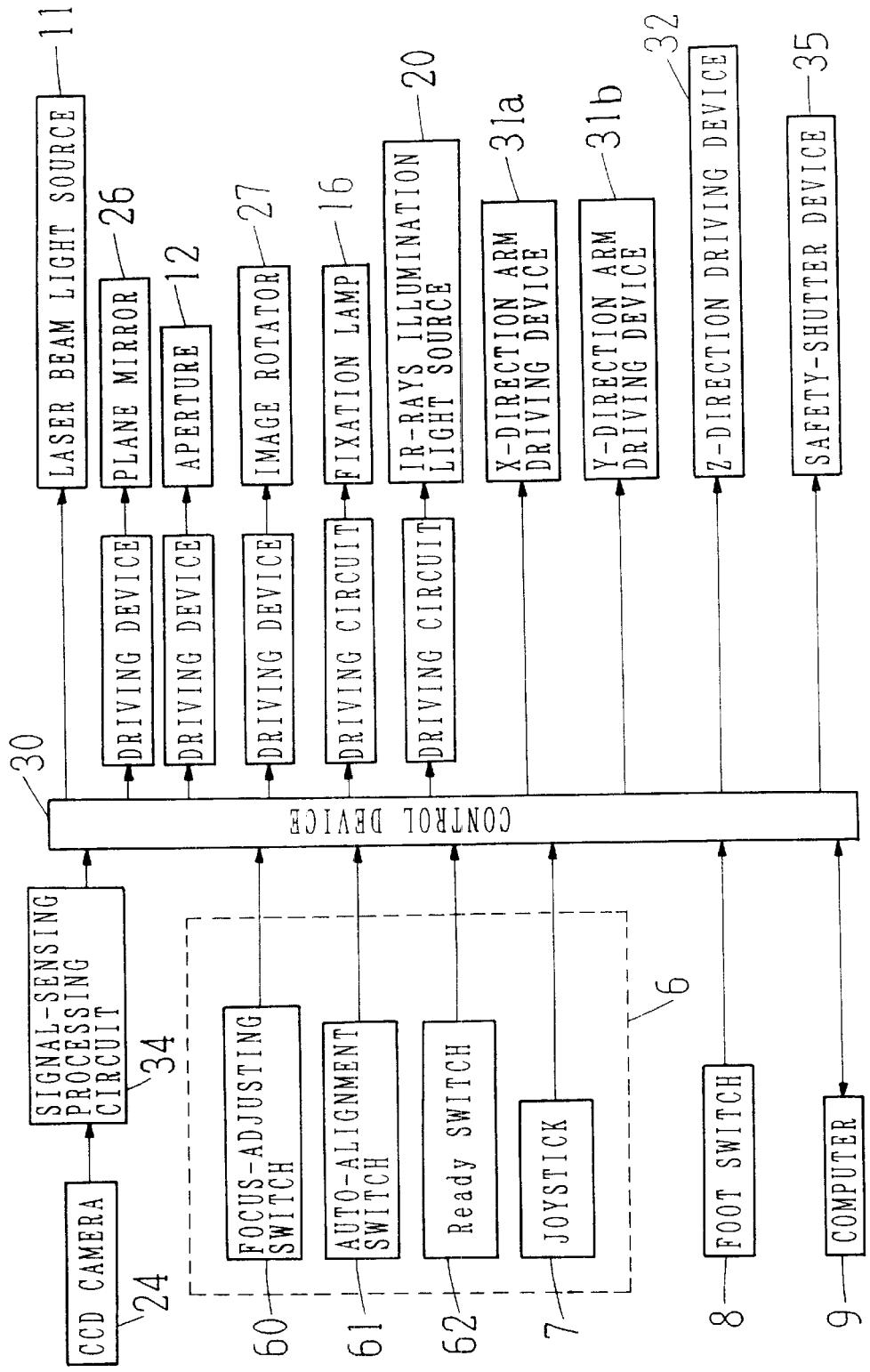
FIG. 6 is a block diagram for a control system of an important part of an apparatus according to the preferred embodiment of the present invention.

FIG. 6 shows a block diagram for a control system of an important part of the apparatus according to the preferred embodiment of the present invention. Reference numeral 30 denotes the control device for controlling whole of the apparatus. The image signal outputted by the CCD camera 24 is converted to binary form by a signal-sensing processing circuit 34, then is given the predetermined process, and then is inputted into the control device 30. The control device 30 detects the pupil position based on signals of light volume every respective all pixel (or the predetermined pixel), then drives and controls respective arm driving devices 31a, 31b and 32.

Figure 9:
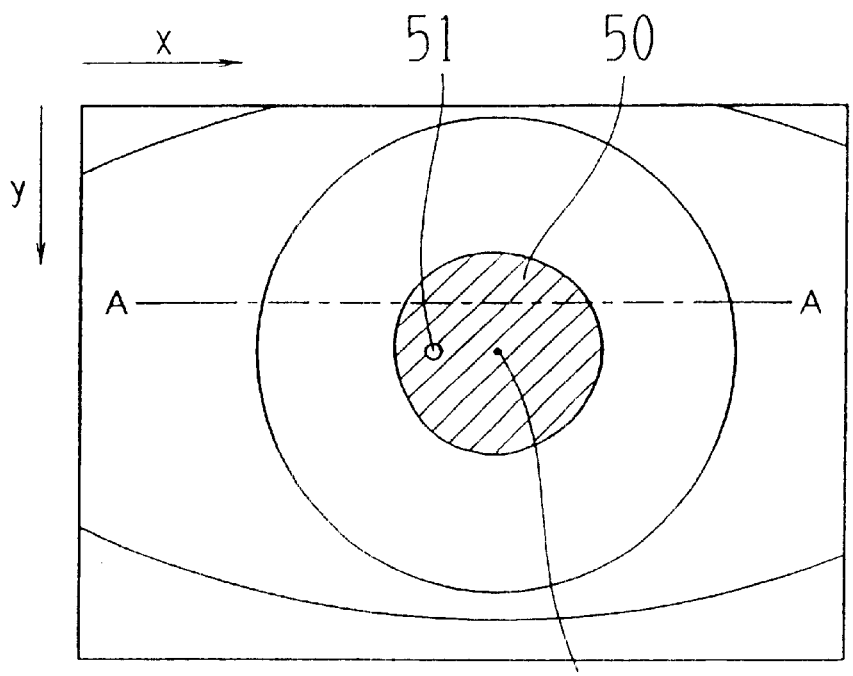
FIG. 9 is a view showing an image of an anterior portion of an eye of a patient photographed by a CCD camera.
Figure 10:
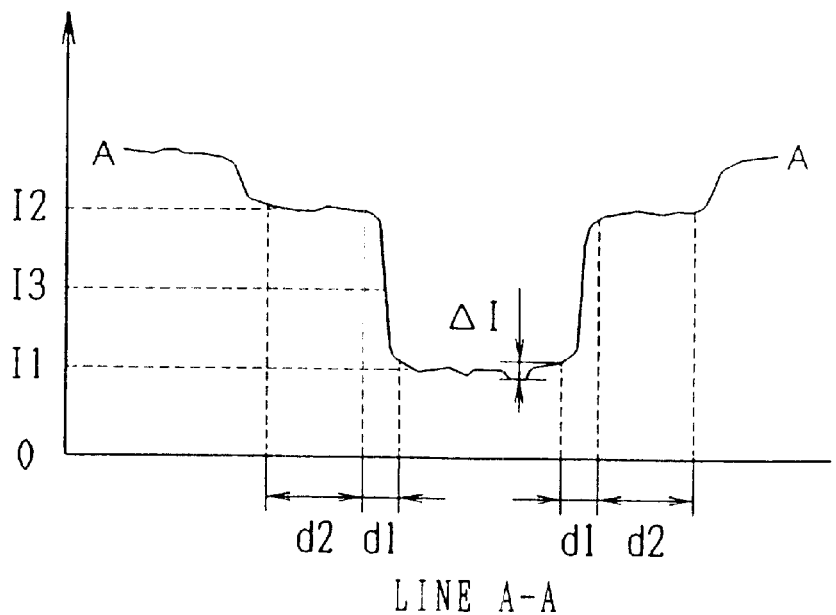
FIG. 10 is a view showing distribution of light volume on line A—A shown in FIG. 9.

Next, method for detecting the pupil position will be described hereinafter. FIG. 9 shows the image of the anterior portion of the eye photographed by the CCD camera 24, FIG. 10 shows distribution of light volume on a scanning line A—A (the line A—A is shown in FIG. 9). The image obtained by the CCD camera 24 is that distribution of light volume depends on the pupil or the iris (except the pupil), therefore, respective levels of light volume for both the pupil and the iris are determined on the basis of the distribution information of light volume.

Determination of levels of light volume for both the pupil and the iris is made as follows. On the distribution information of light volume, volume of reflected light of the pupil is extremely little, therefore the section, of which the level of light volume is the lowest, is extracted among that of all pixel. The pupil is allowed to be considered as being within a range from the lowest level of light volume to a certain level of light volume, therefore the data of the pixel position and the data of light volume being within the predetermined range Δl are obtained with defining the lowest level of light volume as standard. At this time, the data of the pixel position, not adjacent to each other, is preferably excluded. Then obtained data of light volume are averaged, thereby a light volume level l1 of the pupil is determined.

Next, on the basis of above-mentioned data of the pixel position of the pupil, respective data of light volume every pixel positions (or every predetermined intervals) is obtained, where are separated the predetermined range d2 (a range, which is certainly within the iris, may be desired in advance, or may be calculated based on distribution change of light volume) toward both sides from respective positions being separated the predetermined pixel interval d1 (in order to eliminate effect caused by change of light volume of the pupil and the iris) from pixel positions of both edges defined as pupil every scanning line. Then obtained data of light volume are averaged, thereby a light volume level l2 of the iris is specified.

Respective levels of light volume of the pupil and the iris are specified, then threshold level of light volume, which is used for determining a pupil area therebetween, is determined. Difference between the level of light volume of the pupil and that of the iris is large, therefore, a threshold level l3 is determined in the middle therebetween in the preferred embodiment. The data of the pixel position having lower light volume than the threshold level l3 is detected from whole of a screen image, whereby the pupil area 50 is determined (see FIG. 9). After that, xy-coordinates are substituted for distribution of the pixel, then the position of the center of gravity of the area 50 is obtained on coordinates (at this time, related to the axis of coordinates, the process will be easier by defining the center of the screen as (x, y)=(0, 0), and defining the position (0, 0) as the laser beam irradiating optical axis), thereby the obtained position of the center of gravity is defined as the center of the pupil. A relative position of the pupil can be sensed by comparing the optical axis of the detecting optical system which is adjusted so as to be the predetermined positional relationships on the photo-imaging elements of the CCD camera 24 (that is the optical axis of the laser beam irradiating optical system), and the position of the pupil center.

Besides, above-mentioned threshold level l3 (or the level l1 of light volume of the pupil, the level l2 of light volume of the iris) may be determined in advance based on light volume of standard pupil and that of standard iris, simply. Also, this is allowed to be changed and desired by the operator depending on the surgery circumstance.

Referring to above-mentioned sensing of the pupil position, even if the noise light 51, caused by an illumination light or the like, is thrown to the pupil area or an area close to edge of the pupil, then position of the pupil center can be detected stably without being influenced by it so much. Furthermore, the position of the pupil center can be detected precisely without being related to shape of the pupil edge.

The operation of the apparatus, having such architecture as described above, will be described below. The ophthalmic surgery apparatus is connected to a power source and the system is made to run, a menu frame is displayed on the monitor 91 of the computer 9. The ways of the corneal surgery by using the excimer laser beam are PRK (photorefractive keratectomy) operating mode and PTK (phototherapeutic keratectomy) operating mode, in this case, the operator selects the PRK operating mode from the menu frame. The operator inputs several kinds of data such as a refractive power value of the patient's eye 15 and operating conditions or the like, which are inspected beforehand, with the keyboard 92 of the computer 9. The primary body 90 of the computer 9 calculates the ablating amount of the cornea and the like, based on the inputted data. The calculated operating data are inputted to the control device 30 by operating the keyboard 92.

After the input preparations is completed, the operator makes the patient lie down on the bed 10, then places the observation optical system 5 provided the laser beam irradiating orifice above the patient's eye 15. The operator turns on respective light sources, and causes the patient's eye 15 to gaze at the fixation lamp 16.

The operator observes the image of the anterior portion of the patient's eye 15 illuminated by the visible light illuminating light source with the microscope 3, and performs the alignment in X,Y-directions, so that a reticle not shown and the pupil may be the predetermined relationships, by operating the joystick 7, and performs the alignment in Z-direction by operating the focus-adjusting switch 60. The control device 30 causes respective arm driving devices 31a, 31b and 32 to go into run based on signals generated by the joystick 7 and the focus-adjusting switch 60, thereby moves the arm part 2 to X,Y-directions and moves the observing optical part 5 to Z-direction.

Figure 11:
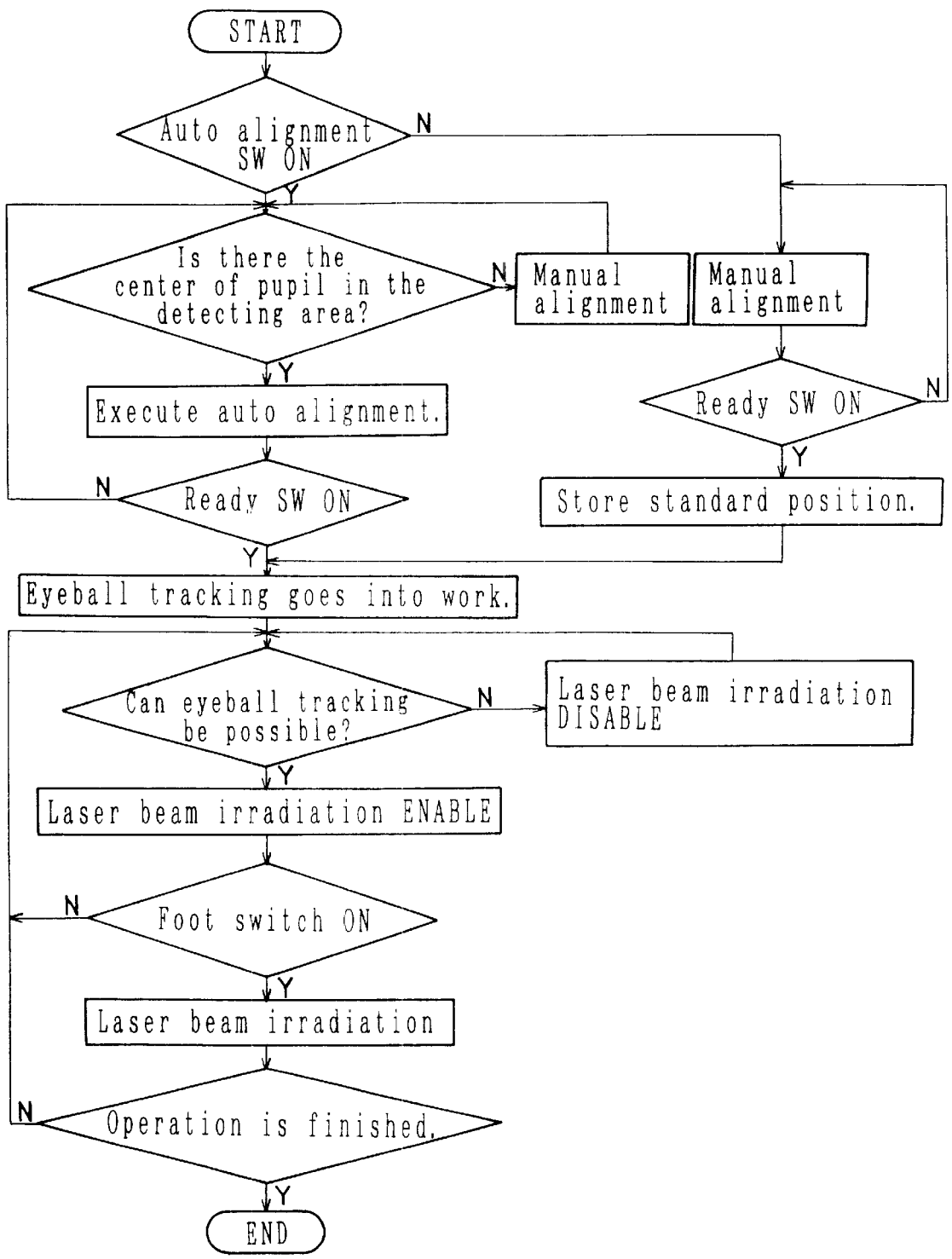
FIG. 11 is a flowchart for illustrating operation of an apparatus of the preferred embodiment of the present invention.

At the time of this alignment, condition for operating is such that the apparatus can select the automatic alignment, which performs the alignment in X,Y-directions based on the detection of the pupil center made by the eyeball position detecting optical system by controlling a working of the arm driving devices 31a and 31b. Once the automatic alignment switch 61 is turned on, the automatic alignment goes into run (see a flowchart shown in FIG. 11). Once the patient's eye 15 enters an area where position of the center of gravity of the pupil area 50 can be detected by the eyeball position detecting optical system (it is can be judged whether the pupil area 50 exists on the center coordinates corresponding to the center of optical axis), then the control device 30 causes the arm part 2 to move to X,Y-directions so that the pupil center obtained as mentioned above may coincide with the laser beam irradiating optical axis.

For example, in the case that coordinates of the pupil center is (x, y)=(40, 0), if the arm part 2 is made to be moved forty-scales of coordinates along X-direction, then the pupil center coincides with the laser beam irradiating optical axis (in the case that the screen center is coincided with the laser beam irradiating optical axis with defining coordinates of the screen center as (x, y)=(0, 0) ).

In the case of performing the laser irradiation under the condition that the laser beam irradiating optical axis coincides with the pupil center as they are, after confirming that the alignment is completed, the Ready switch 62 on the controller 6 is pressed. The control device 30 stores the predetermined position on the photo-imaging elements of the CCD camera 24 (position of the optical axis of the laser beam irradiating optical system) as a standard position, then causes the eyeball tracking mechanism, which moves the arm part 2 so that the standard position may coincide with the pupil center (so that it may enter into the permissible area), to go into run. The position of the pupil center obtained by processing signals from the CCD camera 24 is compared with the standard position at all times, if the patient's eye 15 moves exceeding the predetermined permissible area, then the control device 30 causes the X,Y-directions arm driving devices 31a and 31b to work based on a compared information, thereby the arm part 2 is made to move to X,Y-directions so that the position of the pupil center may enter the permissible area of the standard position. Also, once the eyeball tracking mechanism works in response to a signal inputted by the Ready switch 62, then after confirming that the eyeball is within a range capable of being tracked, a safety-shutter device 35 is released in order to allow performing the laser irradiation by using the foot switch 8.

Then, once the operator steps on the foot switch 8, the control device 30 causes to emit the laser beam. The patient's eye 15 is irradiated with the excimer laser beam via the laser beam irradiating optical system, and the determined amount of the desired area of the cornea Ec is ablated.

At this time, the pupil center, which is deviated extremely, does not detected even if noise light exists at the pupil area of the patient's eye 15 or at the area close to the pupil edge owing to the eyeball position detecting optical system of the apparatus. Thereby, a stable ablation can be achieved with preventing the eyeball tracking mechanism from making an error. Still, in the case that the patient's eye 15 moves exceeding a moving range in X,Y-directions of the arm part 2 during the laser irradiation, the safety-shutter device 35 is made to work in order to intercept the laser irradiation.

In the case that the laser irradiation is performed by aligning the laser beam irradiation optical axis to be an optional position relative to the cornea of the patient's eye 15, the alignment is performed by using the joystick 7 with respect to an target position. After the alignment is completed, once the Ready switch 62 is pressed, then the control device 30 stores coordinates of the pupil center on the photo-imaging elements of the CCD camera 24 as the standard position (in the case of working the automatic alignment, once operating signal of the joystick 7 is inputted, then the coordinates position of the pupil center obtained by offsetting its portion, is stored as the standard position).

In the case that the eyeball moves, the eyeball tracking mechanism, which moves the arm part 2 so that the pupil center may coincide with the stored standard position (so that it may comes into the permissible area), is made to work.

In the preferred embodiment as described above, the detection of the eyeball position calculates the pupil edge based on the information of distribution of light volume of the anterior portion of the eye, and thereby the pupil center is obtained on the basis of the pupil edge, however, since the reflecting light volume from the pupil is extremely little among the reflecting light volume of the pupil, that of the iris, that of the sclera and that of a scillosis, therefore it may be also allowed that the pupil position (deviating direction from the optical axis) is detected according to light-and-shade degree of distribution of light volume on the photo-imaging element of the CCD camera 24. In following, an alignment performed by this detection will be described.

Figure 7:
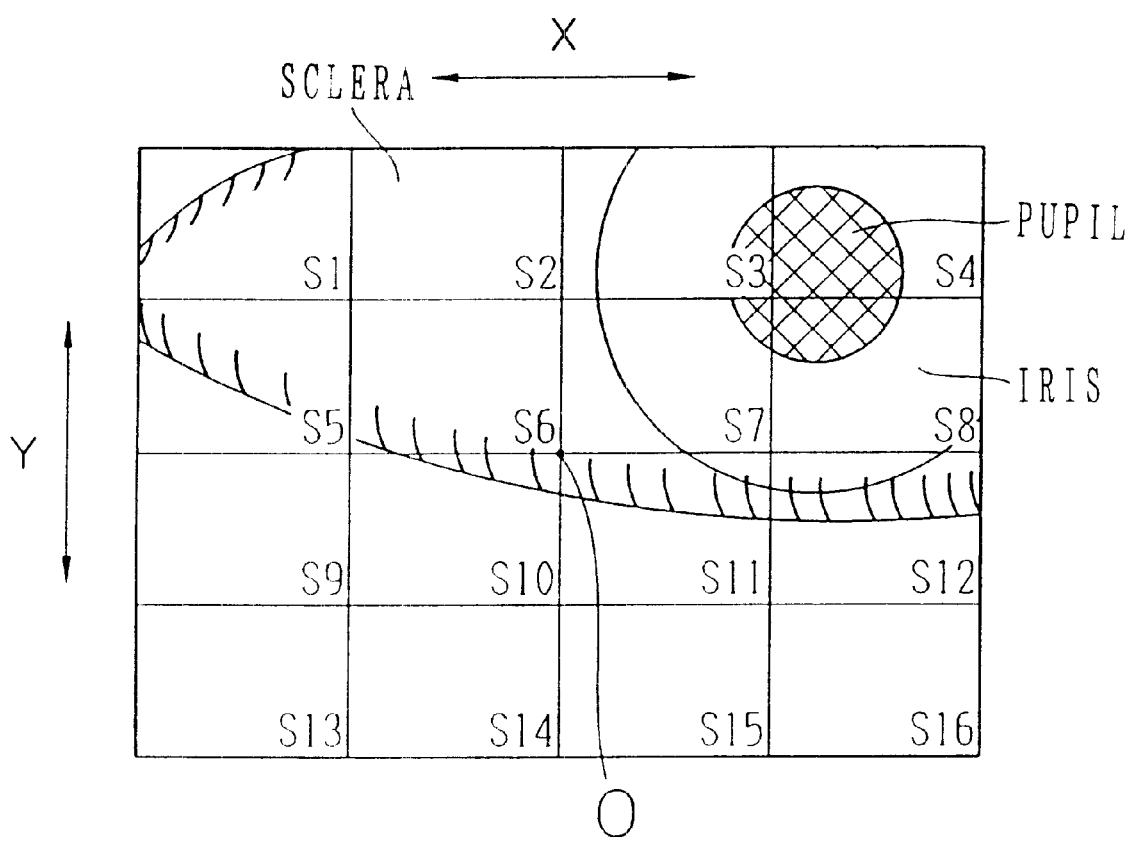
FIG. 7 is a view showing an example for the image divided into 16 areas with the center at an optical axis O relative to a two-dimensional image sent by a CCD camera.

At first, on detecting light-and-shade information of the reflecting light from the anterior portion of the eye, as shown in FIG. 7, the image with the center at the optical axis O is divided into 16 areas (S1 to S16) of 4×4 relative to a two-dimensional image from the CCD camera 24. The positions of the pixel are previously determined, relative to the pixel of respective areas (125 pixel×125 pixel), so that the predetermined number of the pixel (for example, 64 articles), which are defined as objects to be detected for light-and-shade, may equally distributed in the area (all the pixel can be the objects to be detected, however if the required number for detecting are taken as the objects, the processing speed can be faster). Image signals from the CCD camera 24 are digitized by the signal-sensing processing circuit 34, then are given by the predetermined process, and then inputted to the control device 30. Based on the inputted signals, the control device 30 obtains the light-and-shade degree in response to the pixel which are previously determined every respective area. Since the light-and-shade degree every one pixel is converted to binary form, therefore, for example, it can be obtained as the numerical value of the light-and-shade degree of 256 grades from 0 to 255(0 side is the darkest, 255 side is the brightest).

Figure 8:
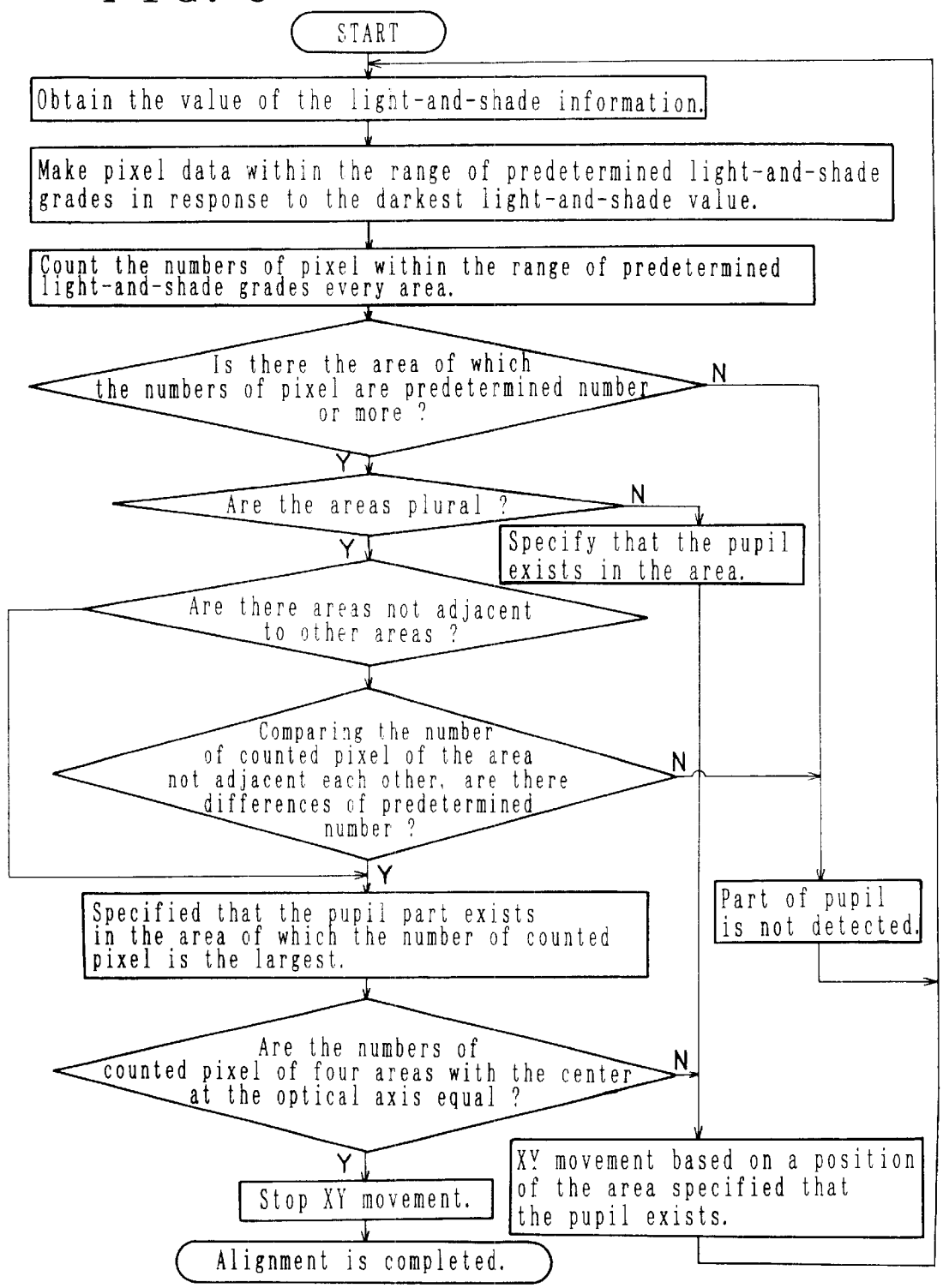
FIG. 8 is a flowchart for illustrating procedure for an automatic alignment which moves an arm part to X,Y-directions based on light-and-shade information.

Then, the operation of the automatic alignment, which detects the pupil based on obtained light-and-shade value, and drives and controls the arm part 2 in X, Y-directions, will be described hereinafter with referring to a flowchart shown in FIG. 8.

If the automatic alignment switch 61 is turned on, the automatic alignment goes into run according to the detection of the pupil based on the light-and-shade value. The control device 30 obtains information of the light-and-shade value on the pixel which is previously determined every respective areas, then extracts the light-and-shade information of the predetermined grades (for example, 20 grades) based on the lowest (the darkest) grade of the light-and-shade value as the standard among them, and counts the number of the pixel within the predetermined range of light-and-shade value in respective areas. Then, it is judged that whether the number of the pixel, which are counted in respective areas, satisfies the predetermined number (for example, 20 articles) or more, or not. In the case that it satisfies the predetermined number, it is judged that the pupil (or the iris around the pupil) exists in the area. In the case that the number of the pixel is little, it is judged that the pupil is not detected, since only a part of the pupil enters into the area, or the section, of which the light-and-shade value is low such as eyelashes, is overlapped on.

In the case that there are the plural areas which satisfy the predetermined number (20 articles) and there are ones which are not adjacent each other among the plural areas, it is judged whether there are differences of the predetermined number (10 articles) or not by comparing the number of counted pixel of the area having largest number with the number of counted pixel of the area not adjacent to the area having largest number. Because, even if there are eyelashes or the like detached from the pupil, in the case that there are some differences between the number of counted pixel, it is taken that the pupil exists in the area which has larger number, and thereby it is distinguished from eyelashes or the like. In the case that there are not the differences of the predetermined number (10 articles), it is taken that the pupil is not detected. In the case that there are the differences of the predetermined number, it is specified that the pupil exists in the area of which the number of counted pixel are the largest, after that, it is judged that whether the number of counted pixel of the 4 members of areas S6, S7, S10, S11, with the center at the optical axis O, are equal (equal within the predetermined range) or not, if there are differences, according to the position of the area of which the pupil exists, the X,Y-directions arm driving devices 31a and 31b are driven and controlled toward the direction to which the differences are dissolved. Once the differences of the number of counted pixel of the 4 members of areas S6, S7, S10, S11 are dissolved completely, driving toward X,Y-directions is made to stop (is not made to drive), thereby the automatic alignment is completed.

Still, on detecting the pupil based on the above-mentioned light-and-shade information, the division of the area in response to the two-dimensional image from the CCD camera 24, it may also be capable of dividing into 4 areas with the center at the optical axis O, simply.

Additionally, concerning control for movement of the arm part 2, it becomes more convenience to use together with movement control based on the pupil center calculated by using the above-mentioned pupil edge. The alignment in large range is performed according to the detection of the pupil based on the light-and-shade information, and when the pupil edge detection is made to be possible, the alignment is performed in detail according to the position of the pupil center based on the detection of the pupil edge. Thereby, if it can be capable of observing the pupil of the patient's eye in the observation optical system, both the alignment in large range and the more accurate alignment are realized.

The present invention may be embodied in other specific forms without departing from the spirit or essential characteristics thereof. For instance, this invention can be enforced without related to the construction of the optical system of the laser beam irradiating optical system such as correction of refractive error or the like, and in the case of the eyeball tracking which based on the position of the optical axis, decided by the operator, of the laser beam irradiating optical system, the alignment operation is also easier by deciding the position in previous inspection and inputting the difference between the position and the pupil center.

The forgoing description of the preferred embodiment of the invention has been presented for purposes of illustration and description. It is not intended to be exhaustive or to limit the variations to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A corneal surgery apparatus for ablating a cornea of an area used for sight of a patient's eye, comprising:
   an observation optical system for observing an anterior portion of the eye;
   a laser beam irradiating optical system for irradiating a laser beam which causes a cornea of the eye ablation;
   illuminating means for illuminating a relatively large area including an iris of the eye;
   a two-dimensional photographing element for photographing a pupil and the iris of the eye illuminated by said illuminating means;
   pupil center detecting means for detecting a pupil center based on pupil information obtained by processing a signal transmitted by said photographing element;
   storage means for storing a predetermined position of said photographing element; and
   moving means for moving said irradiating position, by obtaining deviation between the position of the pupil center detected by said pupil center detecting means and the predetermined position of said photographing element stored by said storage means, so that the detected pupil center position may be placed within a predetermined permissible range of the stored position of said photographing element.

2. A corneal surgery apparatus according to claim 1, wherein the pupil center detecting means comprises arithmetic means for calculating a position of an outer circumference of the pupil based on said pupil information and calculating the pupil center based on the position of the outer circumference of the pupil.

3. A corneal surgery apparatus according to claim 1, wherein said laser beam irradiating optical system includes a generating light source of an excimer laser beam, whereby the cornea of the eye is ablated by said excimer laser beam generated by said light source.

4. A corneal surgery apparatus according to claim 1, further comprising:
   drive signal generating means for generating a signal for driving said moving means so that the position of the pupil center detected by said pupil center detecting means may be placed within the predetermined permissible range of the stored position of said photographing element, at the time when the position of the pupil center is detected; and
   irradiation signal generating means for generating a signal for permitting irradiation of said laser beam in the case that the position of the pupil center detected by said pupil center detecting means is within the predetermined permissible range of the stored position of said photographing element.

5. A corneal surgery apparatus according to claim 1, wherein an optical axis of said observation optical system is coincided with an optical axis of said laser beam irradiating optical system, whereby said observation optical system is also moved by said first and second moving means.

6. A corneal surgery apparatus comprising:
   an observation optical system for observing an anterior portion of an eye of a patient; and
   a laser beam irradiating optical system for irradiating a laser beam which causes a cornea of the eye ablation,
   said corneal surgery apparatus ablates the cornea of an area used for sight of the eye under condition that said irradiating optical system is aligned with the eye, the apparatus further comprising:
   illuminating means for illuminating a relatively large area including an iris of the eye;
   a two-dimensional photographing element for photographing a pupil and the iris of the eye illuminated by said illuminating means;
   pupil center detecting means for detecting a pupil center based on pupil information obtained by processing a signal transmitted by said photographing element;
   storage means for storing a position of the pupil center detected by said pupil center detecting means at the time when alignment before surgery is completed; and
   moving means for moving an irradiating position of said laser beam by said irradiating optical system, by obtaining deviation between the position of the pupil center detected by said pupil center detecting means and the position of the pupil center stored by said storage means, so that the detected pupil center position may be placed within a predetermined permissible range of the stored pupil center position.

7. A corneal surgery apparatus according to claim 6, wherein said laser beam irradiating optical system includes a generating light source of an excimer laser beam, whereby the cornea of the eye is ablated by said excimer laser beam generated by said light source.

8. A corneal surgery apparatus according to claim 6, further comprising:

driving signal generating means for generating a signal for driving said moving means so that the position of the pupil center detected by said pupil center detecting means may be placed within the predetermined permissible range of the position of the pupil center stored by said storage means, at the time when the position of the position of the pupil center is detected; and irradiation signal generating means for generating a signal for permitting irradiation of said laser beam in the case that the position of the pupil center detected by said pupil center detecting means is within the predetermined permissible range of the pupil center stored by said storage means.

9. A corneal surgery apparatus according to claim 6, wherein said pupil center detecting means comprises arithmetic means for calculating a position of an outer circumference of the pupil based on said pupil information and calculating the pupil center based on the position of the outer circumference of the pupil.

10. A corneal surgery apparatus according to claim 1, wherein an optical axis of said observation optical system is coincided with an optical axis of said laser beam irradiating optical system, whereby said observation optical system is also moved by said moving means.

* * * * *

UNITED STATES PATENT AND TRADEMARK OFFICE
CERTIFICATE OF CORRECTION

PATENT NO.    : 6,491,687 B1
DATED         : December 10, 2002
INVENTOR(S)   : Toshifumi Sumiya et al.

It is certified that error appears in the above-identified patent and that said Letters Patent is hereby corrected as shown below:

<u>Title page,</u>
Item [56], U.S. PATENT DOCUMENTS, please change:
"5,684,562  A  *  11/1997  Fuyieda ............ 351/211"

to:

-- 5,684,562  A  *  11/1997  Fujieda ............... 351/211 --

Signed and Sealed this

Twenty-ninth Day of April, 2003

JAMES E. ROGAN
*Director of the United States Patent and Trademark Office*